United States Patent
Euteneuer et al.

(10) Patent No.: US 6,325,814 B1
(45) Date of Patent: *Dec. 4, 2001

(54) CATHETER SUPPORT FOR STENT DELIVERY

(75) Inventors: Charles L. Euteneuer, St. Michael; Christopher R. Larson, St. Paul; Steven P. Mertens, New Hope; Richard C. Mattison, Zimmerman; David J. Blaeser, Champlin; Louis G. Ellis, St. Anthony; Andrew J. Dusbabek, Dayton; Terry V. Brown, Fridley, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/421,076

(22) Filed: Oct. 19, 1999

Related U.S. Application Data

(63) Continuation of application No. 08/807,791, filed on Feb. 28, 1997, now Pat. No. 6,077,273, which is a continuation-in-part of application No. 08/702,150, filed on Aug. 23, 1996, now Pat. No. 6,007,543, and a continuation-in-part of application No. 08/697,453, filed on Aug. 23, 1996, now abandoned.

(51) Int. Cl.[7] ................................................. A61M 29/00
(52) U.S. Cl. ............................................ 606/198; 606/108
(58) Field of Search ................................... 606/108, 194, 606/195, 198

(56) References Cited

U.S. PATENT DOCUMENTS

| | | |
|---|---|---|
| 4,328,056 | 5/1982 | Snooks . |
| 4,338,942 | 7/1982 | Fogarty . |
| 4,423,725 | 1/1984 | Baran et al. . |
| 4,608,984 | 9/1986 | Fogarty . |
| 4,740,207 | 4/1988 | Kreamer . |

(List continued on next page.)

FOREIGN PATENT DOCUMENTS

| | | |
|---|---|---|
| 0 442 657 A2 | 8/1991 | (EP) . |
| 0 529 039 A1 | 2/1993 | (EP) . |
| 0 257 091 B1 | 7/1993 | (EP) . |
| 0 553 960 A1 | 8/1993 | (EP) . |
| 0 274 846 B1 | 2/1994 | (EP) . |
| 0 627 201 A1 | 12/1994 | (EP) . |
| 0 699 451 A2 | 3/1996 | (EP) . |
| 0 707 837 A1 | 4/1996 | (EP) . |
| WO 93/19703 | 10/1993 | (WO) . |
| WO 96/03072 | 2/1996 | (WO) . |
| WO 96/03092 A1 | 2/1996 | (WO) . |

OTHER PUBLICATIONS

Julio C. Palmaz et al., Expandable Intraluminal Graft: A Preliminary Study work in progress[1], Radiology 1985; 156:73–77.

*Primary Examiner*—Justine R. Yu
(74) *Attorney, Agent, or Firm*—Vidas, Arrett & Steinkrau

(57) ABSTRACT

An angioplasty and stent delivery system to facilitate introduction and placement of a stent, including a catheter having an expandable distal portion constructed and arranged for expanding the outer diameter of the catheter from a contracted state to an expanded state: a stent positioned around the distal portion of the catheter having a contracted condition and being expandable to an expanded condition, and being sized in the contracted condition to closely surround the catheter in the contracted state, the expandable distal portion of the catheter including a balloon within which or over which there is included on a catheter shaft at least one axially movable or enlargeable body of a diameter larger than the catheter shaft to which the stent and balloon are fitted, as by crimping, for holding the stent in place until it is released therefrom by expansion of the balloon.

18 Claims, 11 Drawing Sheets

U.S. PATENT DOCUMENTS

| | | |
|---|---|---|
| 4,744,366 | 5/1988 | Jang . |
| 4,848,343 | 7/1989 | Wallstein et al. . |
| 4,875,480 | 10/1989 | Imbert . |
| 4,950,227 * | 8/1990 | Savin et al. ............ 606/191 |
| 5,007,926 | 4/1991 | Derbyshire . |
| 5,026,377 | 6/1991 | Burton et al. . |
| 5,037,392 | 8/1991 | Hillstead . |
| 5,049,132 | 9/1991 | Shaffer et al. . |
| 5,071,407 | 12/1991 | Termin et al. . |
| 5,108,416 * | 4/1992 | Ryan et al. ............ 606/194 |
| 5,116,318 | 5/1992 | Hillstead . |
| 5,158,548 | 10/1992 | Lau et al. . |
| 5,226,880 | 7/1993 | Martin . |
| 5,226,889 | 7/1993 | Sheiban . |
| 5,242,399 | 9/1993 | Lau et al. . |
| 5,290,306 | 3/1994 | Trotta et al. . |
| 5,304,198 * | 4/1994 | Samson ................ 604/194 |
| 5,342,305 | 8/1994 | Shonk . |
| 5,344,402 | 9/1994 | Crocker . |
| 5,344,426 | 9/1994 | Lau et al. . |
| 5,358,487 | 10/1994 | Miller . |
| 5,378,237 | 1/1995 | Boussignac et al. . |
| 5,403,341 | 4/1995 | Solar . |
| 5,405,380 | 4/1995 | Gianotti et al. . |
| 5,409,495 * | 4/1995 | Osborn ................ 606/108 |
| 5,415,664 | 5/1995 | Pinchuk . |
| 5,445,646 * | 8/1995 | Euteneuer et al. ........ 606/198 |
| 5,447,497 | 9/1995 | Sogard et al. . |
| 5,453,090 | 9/1995 | Martinez et al. . |
| 5,458,615 | 10/1995 | Klemm et al. . |
| 5,470,313 | 11/1995 | Crocker et al. . |
| 5,507,768 | 4/1996 | Lau et al. . |
| 5,512,051 | 4/1996 | Wang et al. . |
| 5,534,007 * | 7/1996 | St. Germain et al. ........ 606/108 |
| 5,536,252 | 7/1996 | Imran et al. . |
| 5,571,086 * | 11/1996 | Kaplan et al. ........ 606/108 |
| 5,632,760 * | 5/1997 | Sheiban et al. ........ 606/195 |
| 5,653,691 * | 8/1997 | Rupp et al. ............ 604/96 |
| 5,695,498 * | 12/1997 | Tower ................ 606/195 |
| 5,807,398 | 9/1998 | Shaknovich ............ 606/108 |
| 5,817,102 | 10/1998 | Johnson et al. . |
| 6,123,712 * | 9/2000 | Di Caprio et al. ........ 606/108 |
| B1 4,733,665 | 1/1994 | Palmaz . |

* cited by examiner

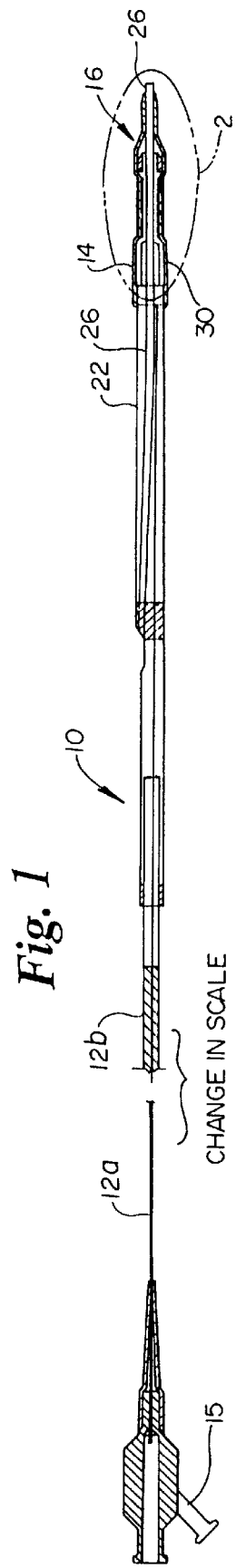
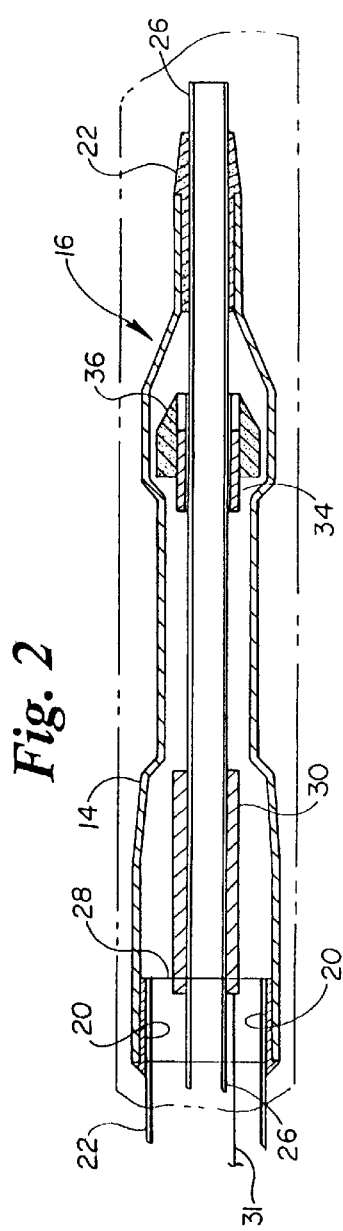
Fig. 1
Fig. 2

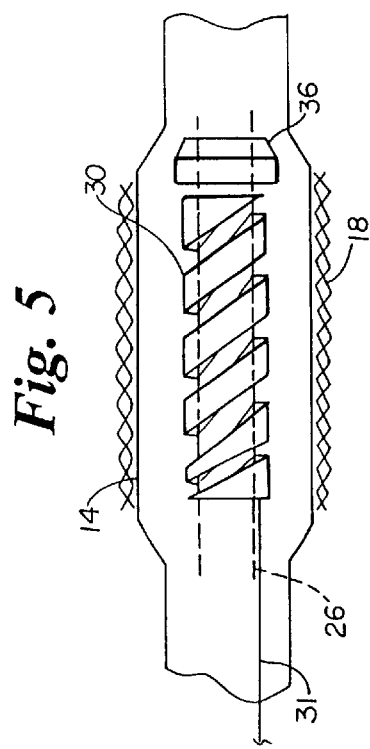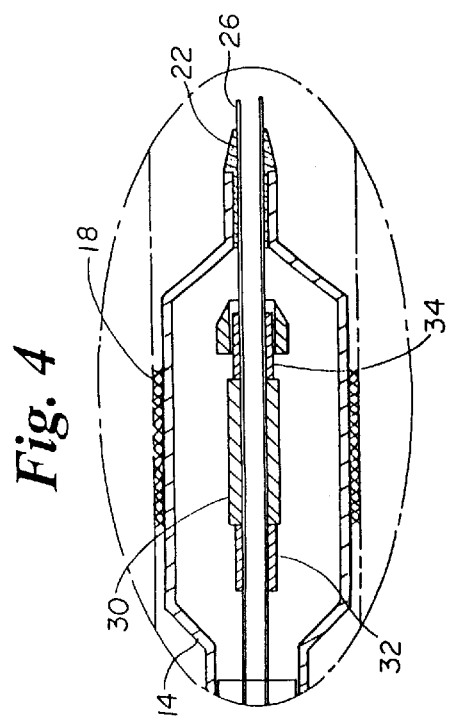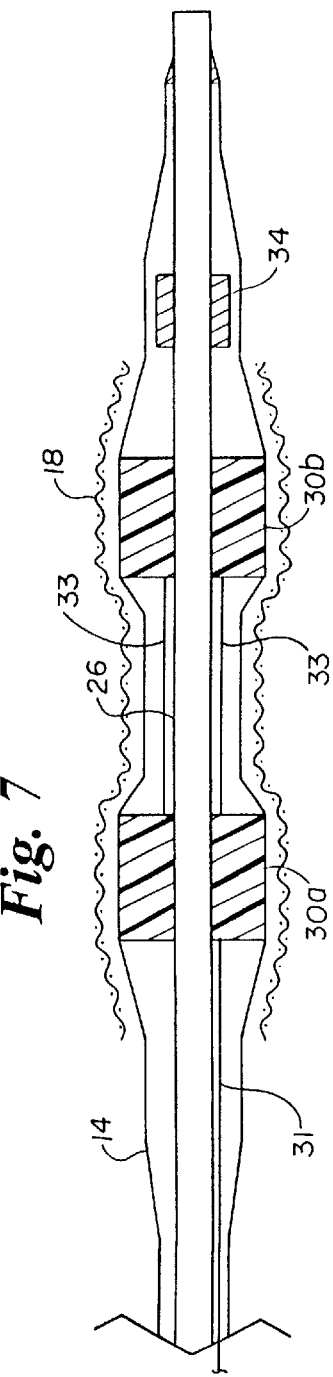

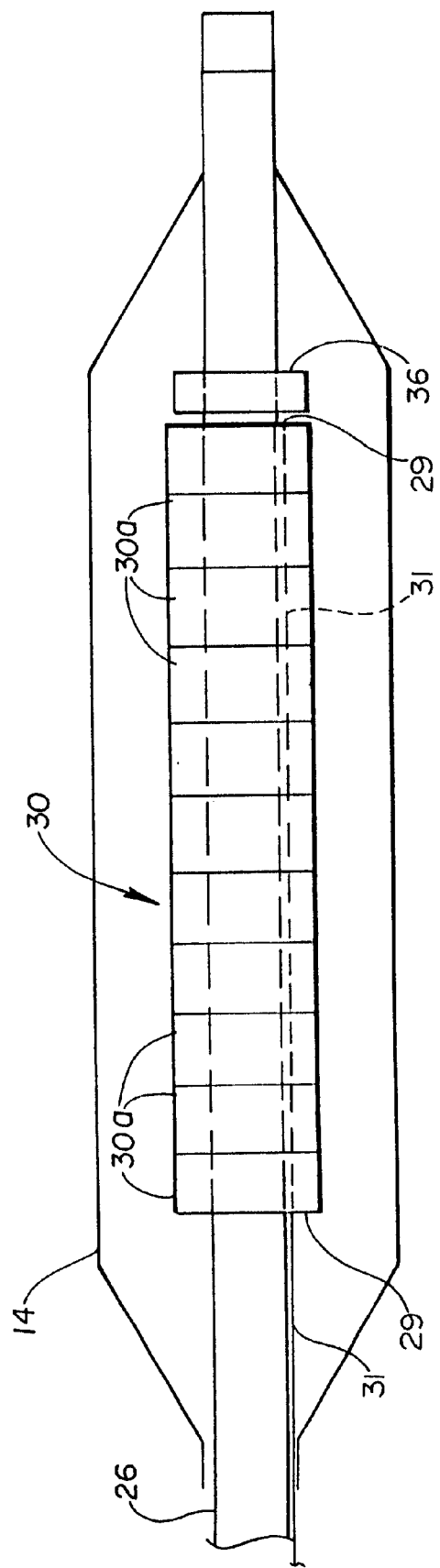

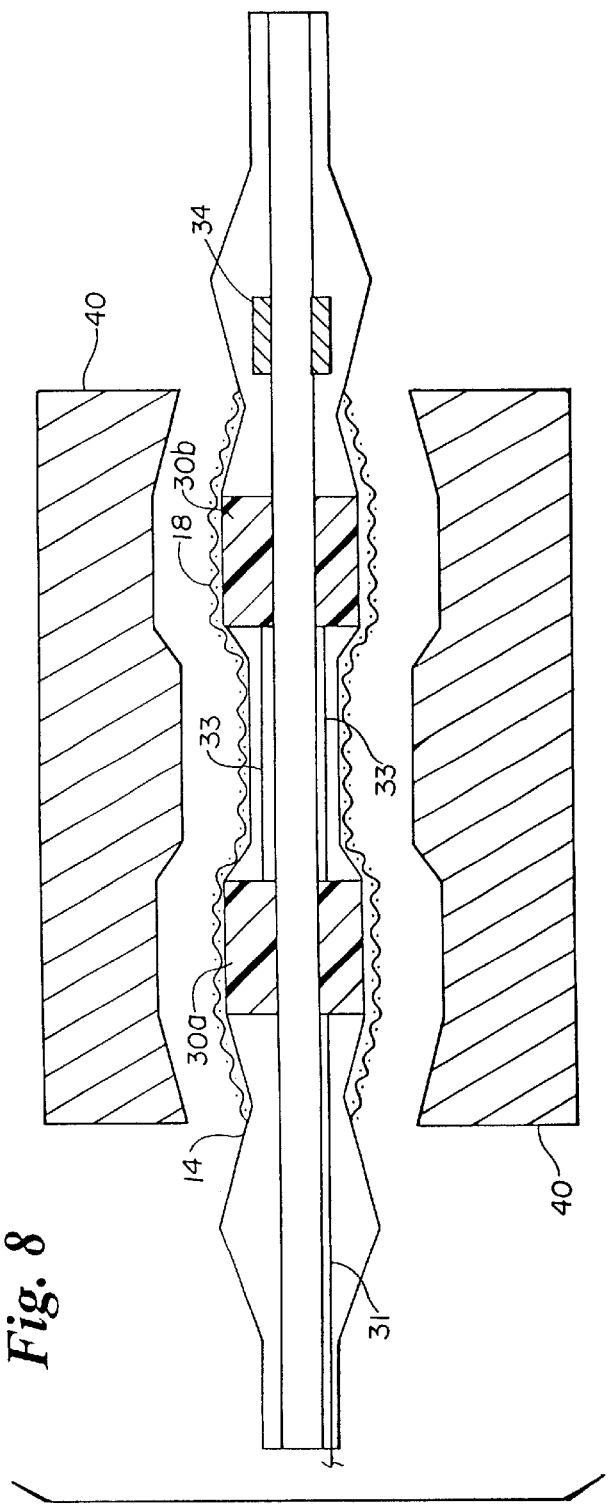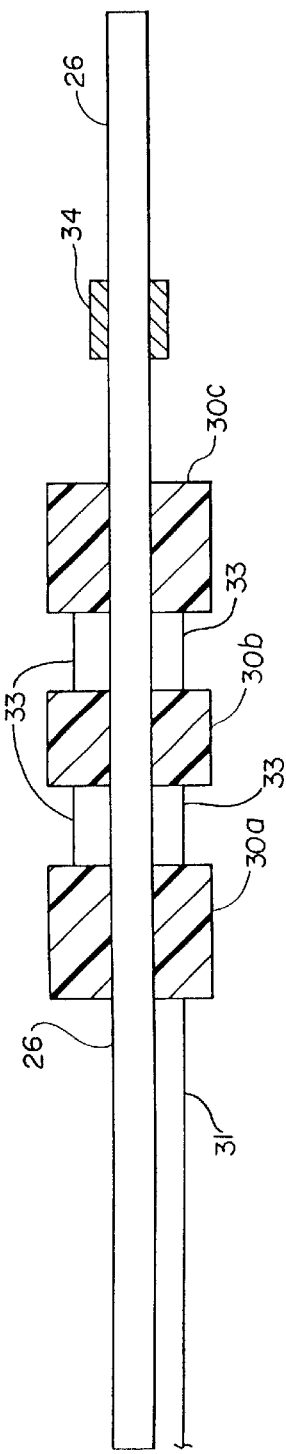

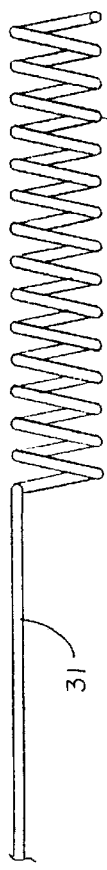
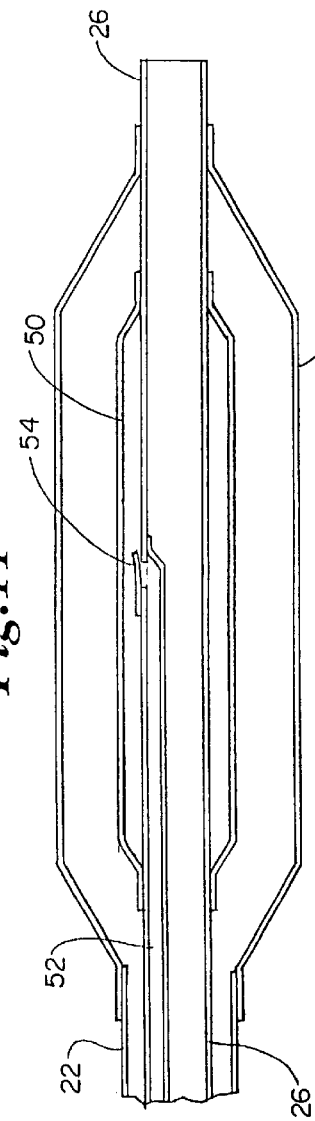
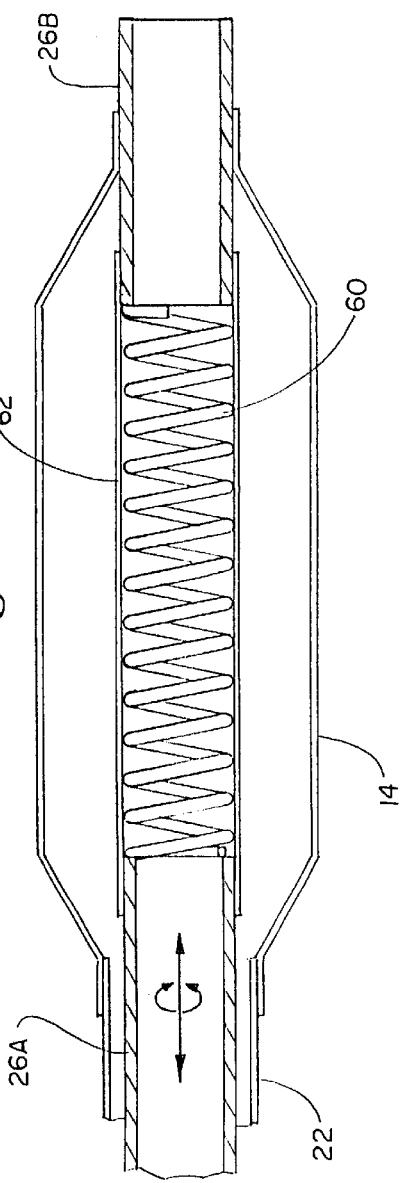
Fig.10
Fig.11
Fig.12

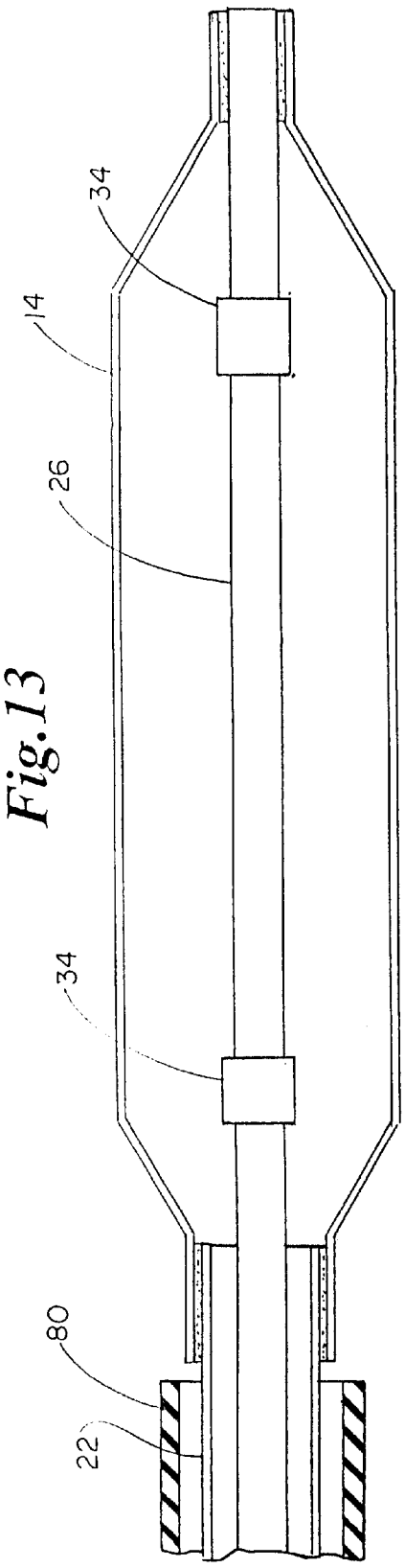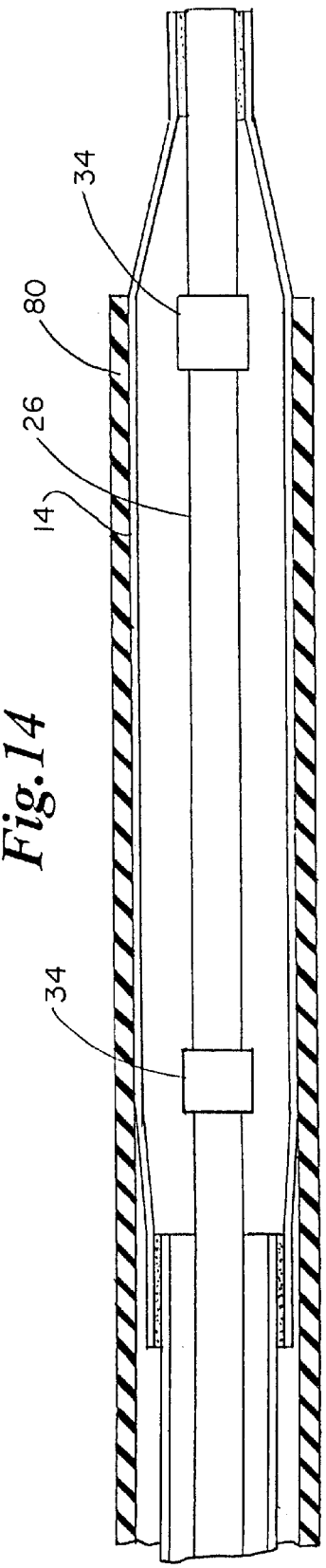

CATHETER SUPPORT FOR STENT DELIVERY

This application is a continuation application of U.S. Ser. No. 08/807,791, filed Feb. 28, 1997, now U.S. Pat. No. 6,077,273, issued Jun. 20, 2000, which is a Continuation-in-Part application based on U.S. Ser. No. 08/702,150 filed Aug. 23, 1996, now U.S. Pat. No. 6,007,543, issued on Dec. 28, 1999, entitled STENT DELIVERY SYSTEM and a Continuation-in-Part of U.S. Ser. No. 08/697,453 filed Aug. 23, 1996, entitled PRE-MOUNTED STENT DELIVERY DEVICE WITH INFLATABLE TUBE COMPONENT, now abandoned, all of which are herein incorporated by reference in their entirety.

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To prevent restenosis and strengthen the area, a physician can implant an intravascular prosthesis, called a stent, for maintaining vascular patency inside the artery at the lesion. The stent is expanded to a larger diameter for placement or implantation in the vasculature, often by the balloon portion of the catheter. Stents delivered to a restricted coronary artery, expanded to a larger diameter as by a balloon catheter, and left in place in the artery at the site of a dilated lesion are shown in U.S. Pat. Nos. 4,740,207 to Kreamer; 5,007,926 to Derbyshire; 4,733,665 to Palmaz; 5,026,377 to Burton et al.; 5,158,548 to Lau et al.; 5,242,399 to Lau et al.; 5,344,426 to Lau et al.; 5,415,664 to Pinchuk; 5,453,090 to Martinez et al.; 4,950,227 to Savin; 5,403,341 to Solar; 5,108,416 to Ryan et al., 5,242,451 to Harada and European Patent Application No. 707 837 A1 to Sheiban, all of which are incorporated herein by reference. A stent particularly preferred for use with this invention is described in PCT Application No. 960 3092 A1, published Feb. 8, 1996, the content of which is also incorporated herein by reference.

The present invention is particularly directed to improved arrangements for catheters of reduced profile for performing angioplasty and for releasably attaching the stent to the catheter to facilitate delivery thereof. The invention is applicable to all the various types of catheters used in such procedures, including rapid exchange types and over-the-wire types.

The various embodiments of the invention disclosed herein are shown in schematic form for clarity and simplicity of illustration. It is anticipated that those familiar with this art will be able to incorporate the invention into actual catheters without difficulty. Similar elements in the Figures are identified by similar or identical numbers.

SUMMARY OF THE INVENTION

This invention concerns catheter apparatus suitable for performing angioplasty and for delivery of stents to body cavities. In general, stents are prosthetic devices which can be positioned within a body cavity, for example, a blood vessel or in some other difficultly accessible place of the body of a living human or animal. The stent prosthesis is formed of a generally tubular body, the diameter of which can be decreased or increased. Stents are particularly useful for permanently widening a vessel which is either in a narrowed state, or internally supporting a vessel damaged by an aneurysm. Such stents are typically introduced into the body cavity by use of a catheter. The catheter is usually of the balloon catheter type in which the balloon is utilized to expand the stent, which is positioned over the balloon for delivery, to place it in a selected location in the body cavity. The present invention is particularly directed to improved arrangements for releasably attaching the stent to the catheter to facilitate delivery thereof. The stent is held in place on the catheter by means of an enlarged mounting body carried within the balloon by the catheter shaft to which the stent and balloon are fitted. The stent is fitted over the balloon, as by crimping. However, according to the invention in some embodiments, the enlarged body is axially movable on the inner shaft of the catheter so that it can be retracted from the stent mounting area to provide a small profile for performing angioplasty. The catheter can then be withdrawn; the enlarged body can be moved into the stent mounting area; the stent can be mounted and the catheter can be re-inserted to implant the stent. In other embodiments, the enlarged body can be arranged to be reducible and enlargeable in size rather than being movable. Alternatively, the movable mounting body may be carried outside the balloon.

A catheter of this type makes possible a method in which, before stent loading with the associated mounting body arranged to provide reduced diameter in the balloon region, the catheter may be used to dilate a lesion or the like. The catheter may be withdrawn and the mounting body may then be selectively manipulated to provide an enlarged diameter in the stent mounting region and a stent may be loaded onto the catheter. The catheter may be re-inserted to implant the stent. The catheter may be withdrawn or left in situ and the mounting body may be manipulated to provide reduced diameter again and the catheter may be used for any post-dilation desired. Also, the catheter may be used multiple times in the procedure for dilation and stent implantation.

BRIEF DESCRIPTION OF THE FIGURES

FIG. 1 is an isometric view, a portion of which is enlarged and in longitudinal section, of a balloon catheter having a mounting body in a retracted position;

FIG. 2 is an even more enlarged view in longitudinal cross-section of the distal end portion of the catheter of FIG. 1;

FIG. 4 is an enlarged cross-sectional view of the distal end portion of the catheter of FIG. 1 similar to that of enlarged view FIG. 3 but showing the balloon in an expanded condition along with the expanded stent;

FIG. 5 is a schematic showing of a preferred mounting body carried by the catheter shaft within the balloon, the body being spirally cut to improve flexibility;

FIG. 6 is a schematic showing in cross-section of another embodiment of the invention with a mounting body positioned to receive a stent but with a stent not yet mounted;

FIG. 7 is a schematic showing of another embodiment of the invention;

FIG. 8 is a schematic showing of a means for conveniently crimping the stent on the embodiment shown in FIG. 5;

FIG. 9 is a schematic showing of yet another embodiment of the invention;

FIG. 10 is a showing of another embodiment of a mounting body according to the invention;

FIG. 11 is a schematic of an enlargeable mounting body which is not axially movable;

FIG. 12 is a schematic of an alternate enlargeable mounting arrangement which is not axially movable;

FIGS. 13 and 14 are schematic showings of yet another embodiment in which the axially movable mounting body is carried outside the balloon;

DESCRIPTION OF THE PREFERRED EMBODIMENTS

Figure 3:
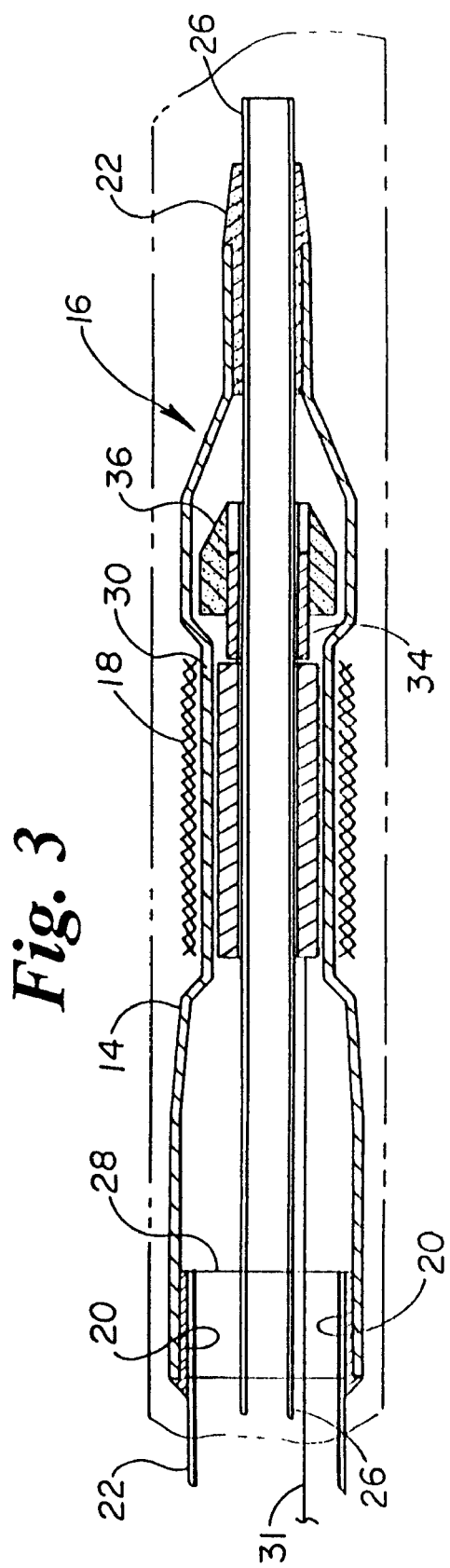
FIG. 3 is similar to FIG. 2 but showing the mounting body advanced to receive a stent mounted on the balloon.

Referring to FIGS. 1–4 an angioplasty and stent delivery catheter system generally indicated at 10 includes a balloon catheter 12 having a balloon 14 on a distal end portion generally indicated at 16. FIG. 1 shows a proximal portion of the catheter at 12a and a distal portion 12b in enlarged view. FIGS. 2 and 3 show the distal end portion 16 in an even more enlarged view. The illustrative catheter 12 is of the type known as a rapid exchange or single operator catheter. However, other types of catheters may be used, such as over the wire and fixed wire types. The balloon 14 is fixed to the catheter 12 by standard means. The balloon is shown in its contracted state in FIGS. 1–3. In FIGS. 1 and 2 the catheter is shown prepared for performing angioplasty and in FIG. 3 it is prepared for stent implantation.

In FIGS. 1 and 2, an axially movable mounting body 30 is shown in a position proximal to the end portion 16 of the catheter where a stent may be mounted. The catheter includes at its proximal end a manifold, generally designated 13, as is known in the art. The manifold includes an inflation port 15 as is known in the art. A wire 31 is attached to body 30 to enable remote (from the proximal catheter end) advancement and retraction of it axially on inner lumen 26 over which it slides. In the retracted position shown in FIGS. 1 and 2, the catheter has a low profile for performing angioplasty.

This position is a retracted position and is selected by operation of a pull wire 31. The retracted position of the mounting body may vary. To maximize the low profile of the distal end 16 of the catheter, the retracted position may be within the outer member 24.

After such a procedure, the balloon is deflated, the catheter is withdrawn and the mounting body is advanced by means of wire 31 to the stent mounting position shown in FIG. 3. A stent 18 may then be fixed about the deflated balloon by crimping it thereto. As can be seen on FIG. 3, the enlarged mounting body may be, as in this instance, substantially the same length as the stent. The stent has a larger expanded diameter which is obtained when the balloon is again expanded in the known manner. That is, the stent is released from the catheter upon expansion of the balloon as shown in FIG. 4 to be placed in a vessel at the desired location. When the balloon is then again deflated, removal of the balloon and catheter may be accomplished, leaving the stent in place. Exemplary dimensions for the inner 26 is a diameter of ½ mm and for body 30 a diameter of ¾ mm.

As is known in the art the balloon is either bonded at its ends by adhesive 20 and 22, respectively to the outer member 24 of the catheter and to the inner member 26 of the catheter in the manner as shown, or is made one-piece with the outer member as is known in the art. The catheter balloon may be inflated by fluid (gas or liquid) from an inflation port extending from a lumen 28 (seen in FIG. 2 and 3) contained in the catheter shaft and opening into the balloon as shown, or by other known arrangements, depending on the design of the catheter. The details and mechanics of balloon inflation and specific overall catheter construction will vary according to the particular design involved in any given instance, and are known in the art per se. Such details are only shown schematically herein. All variations are acceptable for use with this invention.

Any balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application EP0 707 837 A1 and that shown in U.S. Pat. Nos. 5,445,646, or 5,242,451. All of these patents are incorporated herein by reference. Also, shape memory metal stents may be used. As already indicated the stent of PCT Application 960 3092 A1 is particularly preferred.

The stent is typically for example about 16 mm long, while the balloon may be 20 mm long for example. These dimensions, however, are merely representative for illustrative purposes only and are not meant to be limiting. The stent is positioned over the balloon portion of the dilatation catheter and gently crimped onto the balloon either by hand or with a tool such as a pliers or the like to be mounted for delivery as shown in FIG. 3. The crimping may be readily accomplished by the physician during the procedure.

In accordance with this invention, mounting body 30, best seen in FIGS. 2 and 3, is included inside balloon 14 to provide a cushion and/or substrate of enlarged diameter relative to the stent to support and hold the stent and secure it during crimping and the delivery procedure. The mounting body may be axially movable proximally or distally from the position shown in FIG. 3, proximally being preferred.

In the embodiment shown in FIGS. 1–3, mounting body 30 is cylindrical in form and takes the shape of a sleeve axially and slidably carried on inner lumen 26, providing an enlarged area or portion for receiving the balloon and stent when the latter is crimped to the balloon. Marker band 34 may also be included on inner 26 as shown. Any radiopaque material such as gold is useful for this purpose. A stop member 36 of generally conical shape or any other shape may also be included on the marker band 34 as shown to provide additional resistance to stent movement during delivery and to protect the leading edge of the stent during delivery. Polyethylene or the like is suitable for the stop member. Other marker arrangements and stop arrangements may be used as well.

Although, the material of the mounting body may be hard, it is preferably of any deformable thermoplastic material, preferably an elastomer material and more preferably of a relatively resilient elastomer material, e.g., lower durometer silicone. A preferred deformable thermoplastic material is high density polyethylene (HDPE). A preferred lower durometer silicone is in the form of tubing. The deformation of the resilient material of the mounting body when the stent/balloon is crimped to it causes a radial outward force on the stent/balloon increasing the friction therebetween despite any recoil of the stent.

During stent delivery, the balloon catheter is advanced through and positioned in a patient's vasculature so that the stent is adjacent to the portion of the vessel where treatment is to take place. The balloon is inflated to expand the stent to an enlarged diameter. When the stent has reached the desired diameter, the balloon is deflated so that the catheter may be removed leaving the stent in place.

Another embodiment of the invention is shown in FIG. 5. In this embodiment mounting body 30 is a spiral cut elastomer or other suitable material, such as a rigid or flexible plastic, to provide separation for flexibility in that portion of the catheter, allowing more easy movement or tracking around bends. The spiral cut may be only partly through the mounting body or may be all the way through as shown in FIG. 5. Also, while stop member 36 is shown at the distal end portion of the catheter in this embodiment, no stop member may be used.

Another similar version is shown in FIG. 6 which includes a cylindrical mounting body 30 made up of a plurality of separate adjacent rings 30a held together by wire 31 which extends therethrough as shown with stops 29 to secure the rings together. Rings 30a may be individual bodies carried on the sheath or bodies cut from a cylinder to partially separate them or fully separate them. Suitable arrangements may be made to wire 31 at each end of the body 30 to hold the rings together, as shown.

The embodiment shown in FIG. 7 includes another feature based on the geometry of the mounting body for further securing the stent upon crimping. This feature is referred to herein as "interlocking". That is, the stent may be interlocked to the mount so that the stent cannot slide proximally or distally on the balloon unless it is deformed, such as by expansion. This can be seen by perusing the structure shown in FIG. 7 which includes the inner 26 having a two-piece mounting body made up of spaced mounting bodies 30a and 30b. These bodies are connected to each other by connection means 33 which may be a separate or integral cylindrical body of lesser diameter or may be one or two or more relatively rigid wire members as shown. The spacing between bodies 30a and 30b allows portions of the stent 18 and balloon 14 to be depressed or inserted between the bodies upon crimping of the stent thus forming an interlock against sliding of the stent axially or longitudinally before the stent is released.

The interlock formation or crimping is readily accomplished by any suitable means such as a two-piece die 40 shown in FIG. 8 or the like.

FIG. 9 demonstrates that more than a two-piece mounting body arrangement may be used if desired. In this embodiment, the mounting body is comprised of three spaced interconnected bodies 30a, 30b and 30c on the inner 26. Preferably in the embodiments of FIGS. 7 and 9, the mounting bodies will be ring-like in shape or cylindrical in shape although other configurations will be readily apparent to those familiar with this art.

Referring now to FIG. 10, another embodiment of a movable mounting body 30 is shown in the form of a rigid coil of plastic, metal or the like having a control wire 31, preferably integral therewith. When in the metal form, the coil may be coated with a polymer such as polyethylene or PTFE or enclosed in a polymeric sheath of similar material. The coil may be slidably received on the inner 26 similar in arrangement to that shown in the preceding Figures.

As already indicated, an alternate arrangement may be used in which the mounting body, instead of being movable, is designed to be enlargeable and reducible or collapsible, while remaining in a fixed position in the stent mounting area of the catheter. FIGS. 11 and 12 are directed to such an arrangement.

In FIG. 11, an inner balloon 50 of smaller diameter than outer balloon 14 is mounted on the inner 26. Balloon 50 may have a separate inflation conduit 52 inside inner 26, preferably including a valving arrangement 54. Valve 54 may be a one-way valve allowing only inflation of balloon 50 if desired. However, inner 26 may serve as the inflation conduit as well. In addition to fully inflat the balloon, inner balloon 50 may also be partially inflated.

Figure 19:
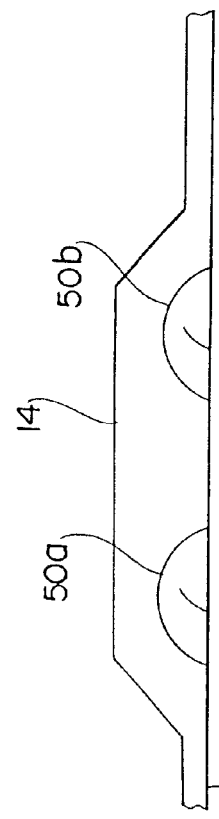
FIGS. 19 and 20 are modified versions of the embodiment shown in FIG. 11.
Figure 20:
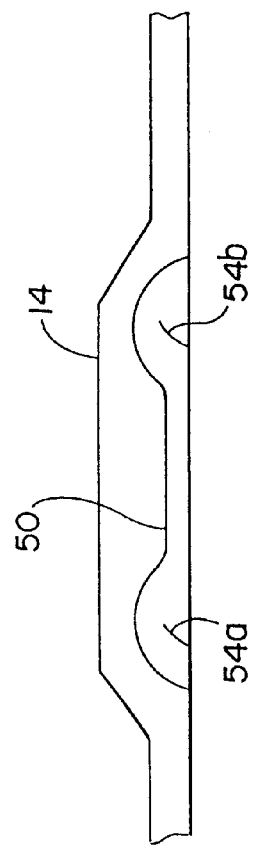

FIG. 19 shows a modification to FIG. 11 in which two inner balloons 50a and 50b are included. FIG. 20 shows a modification in which two inflation valves 54a and 54b are included.

Figure 21:
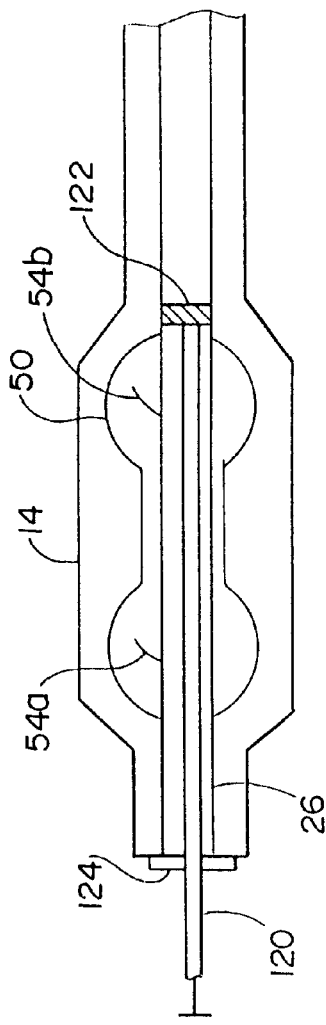
FIG. 21 shows a version of the embodiment shown in FIG. 11 in which a syringe is inserted in to the distal end of the liner of the catheter.

FIG. 21 shows a full arrangement of inner balloon 50 in which a syringe 120 is inserted into the distal end of the liner 26 of the catheter. The syringe has at its ends blocks 122 and 124 to enable local pressurization of inner 26 to inflate balloon 50.

Figure 17:
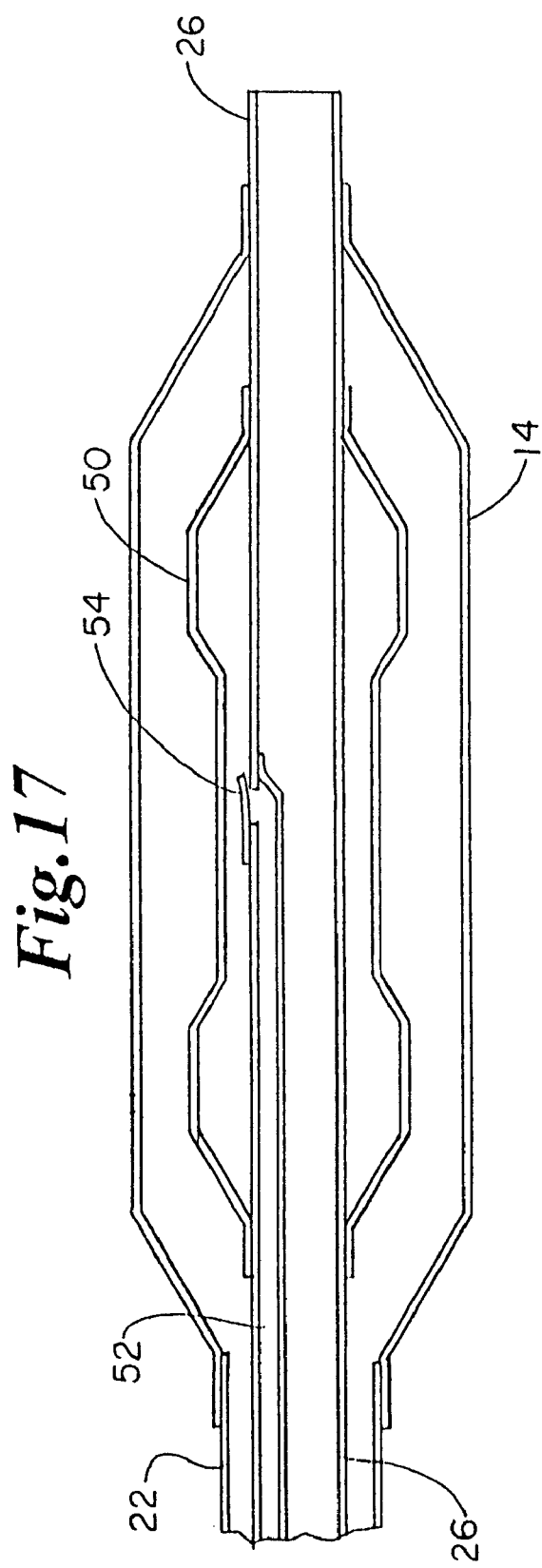
FIGS. 17 and 18 are a modified version of the embodiment shown in FIG. 11.
Figure 18:
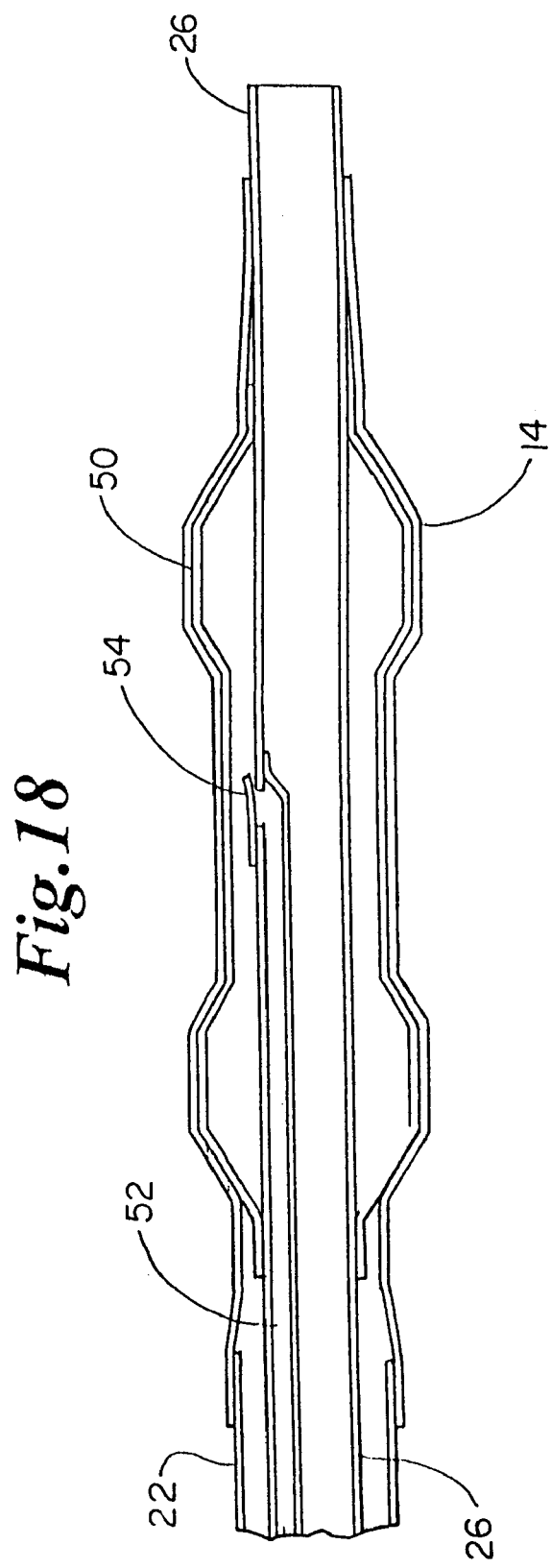

FIGS. 17 and 18 show an inner balloon 50 similar to the arrangement of FIG. 11 but the balloon 50 in FIG. 17 has a narrow center portion and wide ends to provide a mounting shape similar to that of FIG. 7. In FIG. 17, balloon 50 is inflated and balloon 14 is partially inflated. In FIG. 18, balloon 50 is inflated and balloon 14 is uninflated ready for stent loading. Balloon material is preferably a polyethylene or urethane elastomer such as Tecoflex or Tecothane from Thermedics.

Referring to FIG. 12, an alternate embodiment is shown in which the proximal portion of the inner 26 is axially movable while the distal portion 26b is fixed with respect to the catheter. In between portion 26a and portion 26b is a coil spring 60 inside a flexible sheath 62 of PTFE or the like. Portion 26b of the inner is attached to balloon 14 at the very distal end portion of the catheter. Portion 26a is movable axially within the outer 22. Thus, if 26a is pushed in the distal direction and held to compress coil 60, the coil will enlarge in diameter to provide an enlarged mounting area for a stent. Twisting the inner to twist the coil will enhance enlargement. Alternatively, coil spring 60 may be replaced by a braided element.

Also, by providing different pitch over the length of the coil it can be made to enlarge more in some regions than in others. For example, if the coil windings are closer together in the center portions than in the end portions, when the coil undergoes compressing, the two end portions will enlarge in diameter more than the center portion to provide a mount similar to that of FIG. 7.

Referring now to FIGS. 13 and 14, another embodiment is shown which is alternative to the earlier described embodiments which are inside the balloon on the catheter. In this embodiment a sheath 80 is carried on the outside of the catheter. Sheath 80 is elastomeric and is axially movable from a stent mounting position as shown in FIG. 14 to a position remote from the stent mounting position, such as the retracted position as shown in FIG. 13. In the position shown in FIG. 13, balloon 14 may be inflated and deflated. In the position shown in FIG. 14, balloon 14 will be deflated for low profile. Sheath 80 when over the balloon as in FIG. 14 acts to increase the profile of the catheter to facilitate crimping a stent thereto during deployment of the stent, sheath 80 will expand with balloon 14 to facilitate inflation and during deflation the elastomer sheath will return to its original dimension. An elastomer material which is presently preferred is Tecothane, a tradename for a thermoplastic polyurethane available from Thermedics, Inc., of Woburn, Mass. It may be about 0.003 inches thick, for example.

Figure 15:
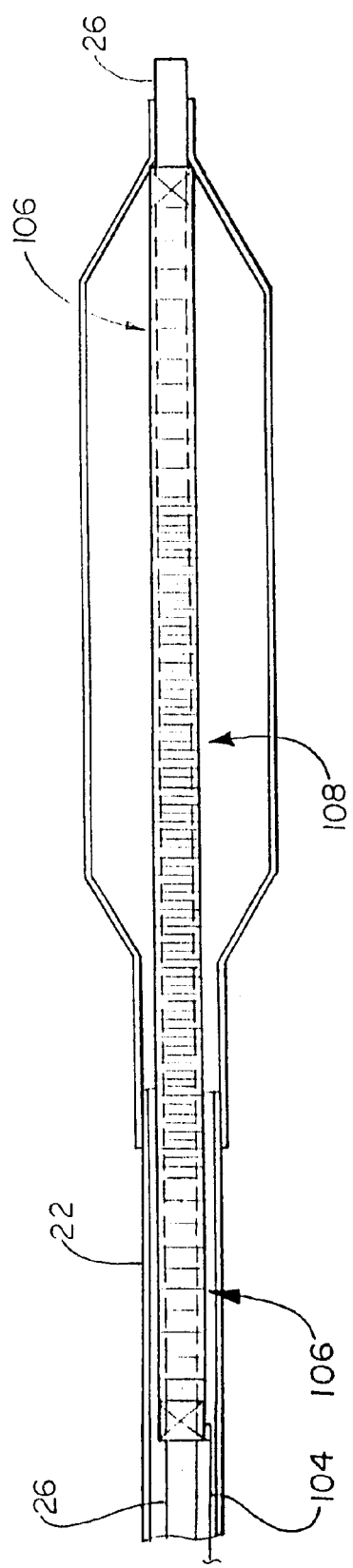
FIGS. 15 and 16 are schematic showings of still yet another embodiment of the invention.
Figure 16:
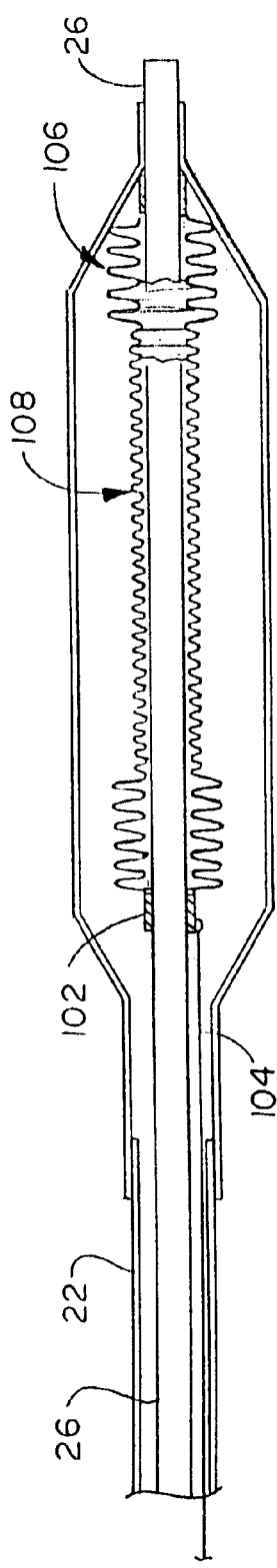

With respect to FIGS. 15 and 16, a further embodiment of the invention is shown in which inner 26 carries a mounting body 30, the distal end 100 of which is secured or fixably attached to inner 26, as by any suitable adhesive. The remainder of body 30 is slidable over inner 26 as by the application of compression in the distal direction at the proximal end 102. This may be accomplished by push wire 104 which extends to the proximal end of the catheter for remote manipulation as is known in the art.

Mounting body 30 is accordion folded with more widely spaced folds at the end portions 106, than at the central portion 108. Thus, as can be seen in FIG. 15, a relatively low profile is provided without compression for normal angioplasty use. When a stent is to be mounted (not shown), compression by means of push wire 104 will result in a configuration of enlarged diameter of body 30 as shown in FIG. 16 to provide a mount similar to that of FIG. 7 in general configuration. If the spring is uniform over the body, it sill enlarge uniformly, similar to the inner balloon of FIG. 11. The Figures are schematic in form but the concept can be readily appreciated.

As an alternative to a folded construction, the body may be of braided construction to achieve the same operation.

Also, this form of body 30 may be inserted into a two piece inner 26 similar to the arrangement shown in FIG. 12. In all of these arrangements, the accordion folded body material may be of any suitable polymer, such as polyethylene. For example, tubing having a wall thickness of about 0.002 inches may be used. The accordion folds or pleats may be readily formed in such tubing by means of a pressure mold containing spaced blades placed in a heated chamber.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system comprising a catheter having a inner shaft and expandable inflatable means associated therewith at a distal part of the inner shaft and including mounting and retaining means for receiving a stent on the expandable means for radial expansion of the stent, the mounting and retaining means being associated with the inflatable means and being constructed and arranged for selectively providing an enlargeable mounting body for receiving the stent, wherein the inner shaft and the mounting body are inside the inflatable means and wherein the enlargeable mounting body is capable of being remotely enlarged and is at least partially axially movable relative to the inner shaft.

2. The stent delivery system of claim 1, wherein the mounting body is carried on and surrounding the shaft inside the inflatable means whereby the diameter of the shaft and inflatable portion may be increased at the distal part of the shaft for facilitating the mounting and retaining of the stent.

3. The stent delivery system of claim 2 further including means for moving at least a portion of the mounting body relative to the inner shaft, whereby moving the mounting body relative to the inner shaft enlarges the mounting body.

4. The stent delivery system of claim 3 wherein the mounting body is of a material which resiliently deforms under radial pressure.

5. The stent delivery system of claim 4 wherein the material is elastomeric.

6. The stent delivery system of claim 4 wherein the material comprises high density polyethylene.

7. The stent delivery system of claim 4 wherein the material comprises silicone.

8. The stent delivery system of claim 3 wherein the mounting body is adjustable to receive a stent and a stent is crimped to the mounting and retaining means over the inflatable means for delivery.

9. The stent delivery system of claim 3 including at least one marker band.

10. The stent delivery system of claim 8 wherein the inflatable means comprises a balloon.

11. The stent delivery system of claim 3 wherein the mounting body is a sleeve having a length, a proximal end and a distal end and having radial pleats extending over at least a portion of sleeve's length, the distal end of the sleeve being secured to the inside shaft, and a means for compressing the sleeve's body from its proximal end and attached thereto.

12. The stent delivery system of claim 11 wherein the pleats of certain portions of the body are spaced differently to provide regions of different enlargement.

13. The stent delivery system of claim 1, the enlargeable mounting body having a first end and a second end, wherein the first end is stationary relative to the inner shaft and the second end is movable relative to the inner shaft, wherein the enlargeable mounting body is enlarged by moving the second end of the enlargeable mounting body relative to the inner shaft.

14. The stent delivery system of claim 13, wherein the enlargeable mounting body is enlarged by shortening the enlargeable mounting body.

15. The stent delivery system of claim 13, wherein the enlargeable mounting is enlarged by twisting the mounting body.

16. A method of changing the profile of a balloon catheter for improving the mounting of a stent thereon and providing a catheter for multiple use, comprising the steps of:

providing a balloon catheter of relatively low profile adapted and rearranged for use in an angioplasty procedure, the balloon catheter having an inner shaft and a balloon;

providing a stent mounting body having a first length onto the inner shaft, within the balloon;

shortening the length of the stent mounting body into a position on the inner shaft associated with the balloon for receiving a stent and enlarging the catheter profile at that position, and mounting a stent on the balloon and mounting body at that position.

17. In a balloon catheter apparatus, the method of enlarging the catheter profile for facilitating the mounting of a stent thereon, comprising:

selectively providing an enlargeable mounting body within the balloon in a position to receive a stent; and enlarging the enlargeable mounting body from a position on the balloon catheter apparatus remote from the enlargeable mounting body, wherein the enlargeable body is enlarged by shortening its length.

18. The method of claim 17 wherein the enlargeable body is enlarged for receiving the stent by compressing the enlargeable body.

* * * * *